United States Patent
Fujishige et al.

(10) Patent No.: US 6,507,642 B2
(45) Date of Patent: Jan. 14, 2003

(54) COLLIMATOR CONTROL METHOD AND APPARATUS, AND X-RAY CT APPARATUS

(75) Inventors: Takashi Fujishige, Tokyo (JP); Masatake Nukui, Tokyo (JP); Makoto Gohno, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/950,997

(22) Filed: Sep. 12, 2001

(65) Prior Publication Data

US 2002/0076000 A1 Jun. 20, 2002

(30) Foreign Application Priority Data

Nov. 9, 2000 (JP) .......................................... 2000-341412

(51) Int. Cl.$^7$ ................................................. G21K 1/04
(52) U.S. Cl. .......................... 378/151; 378/150; 378/19
(58) Field of Search ................................. 378/150, 147, 378/151, 19, 20, 145, 205, 207, 98.11, 98.12

(56) References Cited

U.S. PATENT DOCUMENTS 5,469,429 A  * 11/1995  Yamazaki et al. ............. 378/19
6,056,437 A  *  5/2000  Toth ........................... 378/205

* cited by examiner

Primary Examiner—Drew A. Dunn
Assistant Examiner—Elizabeth Gemmell
(74) Attorney, Agent, or Firm—Moonray Kojima

(57) ABSTRACT

In order to control a collimator so that an X-ray impingement position on an X-ray detector is kept constant, an error of the impingement position of a fan-shaped beam (400) in the direction of side-by-side arrangement of a plurality of detector element rows in a detector element array (24) is detected (101), and the collimator is controlled (103) based on the detected error so that the impingement position of the fan-shaped beam is kept at a constant position.

26 Claims, 9 Drawing Sheets

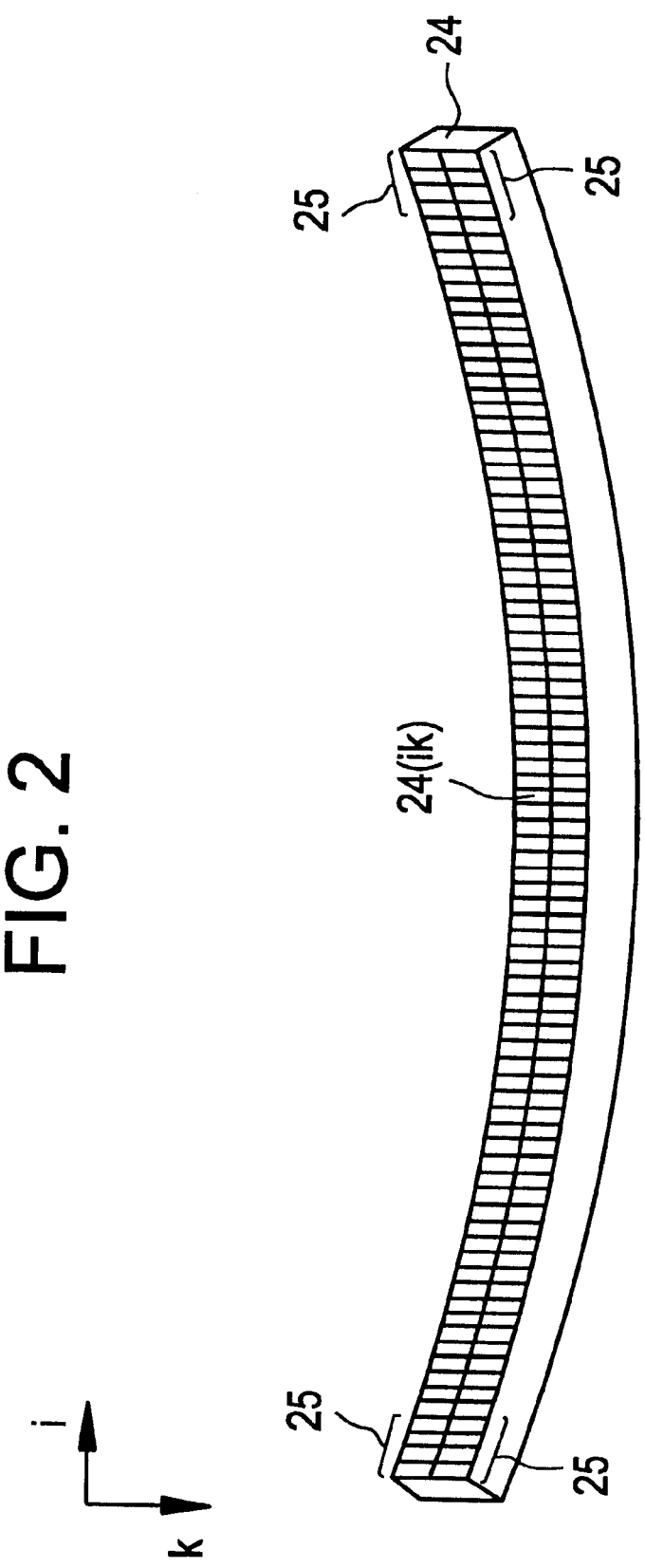

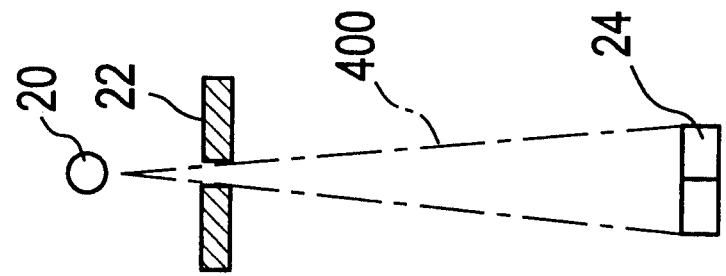
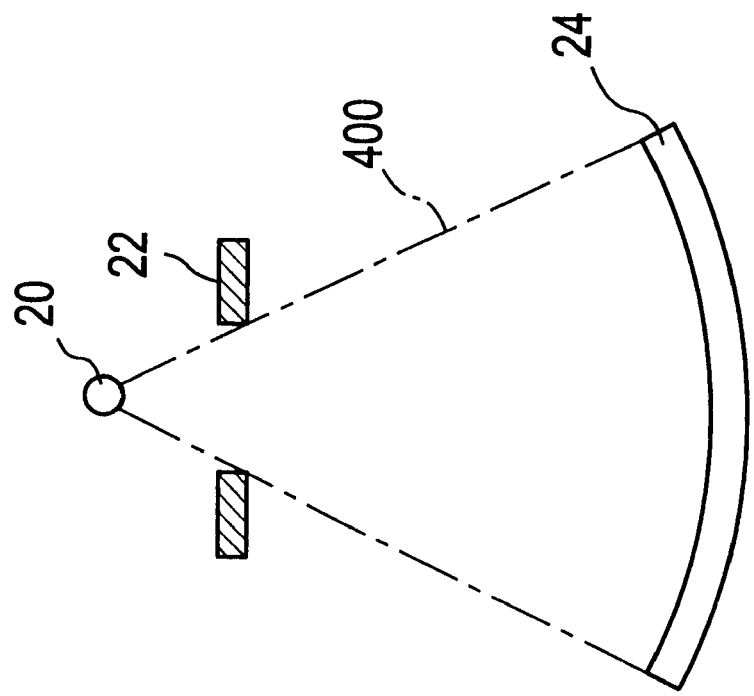

COLLIMATOR CONTROL METHOD AND APPARATUS, AND X-RAY CT APPARATUS

BACKGROUND OF THE INVENTION

The present invention relates to a collimator control method and apparatus and an X-ray CT (computed tomography) apparatus, and more particularly to a method and apparatus for controlling a collimator for defining an impingement position of an X-ray beam on an X-ray detector, and an X-ray CT apparatus comprising such a collimator control apparatus.

An X-ray CT apparatus acquires signals of transmitted X-rays for a plurality of views with respect to an imaging object by an X-ray emitting/detecting apparatus, and produces a tomographic image of the object by an image producing apparatus based on the signals of transmitted X-rays.

The X-ray emitting apparatus forms a cone-shaped X-ray beam emitted from a focus of an X-ray tube into a fan-shaped X-ray beam by a collimator, and projects the fan-shaped X-ray beam toward an imaging space.

The X-ray detecting apparatus detects the X-rays passing through the imaging space by a multi-channel X-ray detector that comprises a multiplicity of X-ray detector elements arranged in an array along the extent of the fan of the X-ray beam. Such an X-ray emitting/detecting apparatus is rotated (or scans) around the object to acquire the signals of transmitted X-rays for the plurality of views.

One of several types of the multi-channel X-ray detector is a detector element array comprising a plurality of detector element rows arranged side by side in the thickness direction of the fan-shaped X-ray beam to simultaneously receive an X-ray beam by the plurality of rows of the detector element array. Since such an X-ray detector can obtain X-ray detected signals for a plurality of slices together in one scan, it is used as an X-ray detector for efficiently performing a multi-slice scan.

Such X-ray detectors include an X-ray detector element array that comprises two rows and obtains projection data for two slices together. In such an X-ray detector, two rows of the array are disposed adjacent to each other in parallel, and illuminated by an X-ray beam equally divided in the thickness direction of the X-ray beam. The thicknesses of the X-ray beam impinging upon the two rows of the array at an isocenter of the object determines the slice thicknesses of tomographic images.

The X-ray tube undergoes an X-ray focus shift caused by thermal expansion or the like due to a temperature rise during use, which shift appears as displacement in the thickness direction of the X-ray beam after passing through an aperture of the collimator. When the X-ray beam shifts in the thickness direction, the division of the thickness of the X-ray beam becomes unequal between the two rows of the array. Equality between the slice thicknesses of two tomographic images is therefore lost.

SUMMARY OF THE INVENTION

It is therefore an object of the present invention to provide a collimator control method and apparatus for keeping a constant X-ray impingement position on an X-ray detector, and an X-ray CT apparatus comprising such a collimator control apparatus.

(1) In one aspect for solving the aforementioned problem, the present invention is a collimator control method, comprising the steps of: forming X-rays emanating from a focus of an X-ray tube into a fan-shaped beam by a collimator, and projecting the fan-shaped beam onto a detector element array comprising a plurality of detector element rows arranged side by side in the thickness direction of the fan-shaped beam, each of which detector element rows comprises a plurality of X-ray detector elements disposed in line in the extent direction of the fan-shaped beam; detecting an error between an impingement position of the fan-shaped beam and a predetermined impingement position in the direction of the side-by-side arrangement of the detector element rows on the detector element array; and controlling the collimator based on the detected error so that the impingement position of the fan-shaped beam coincides with the predetermined impingement position.

(2) In another aspect for solving the aforementioned problem, the present invention is a collimator control apparatus, comprising: an X-ray tube for generating X-rays emanating from a focus; a collimator for forming the X-rays into a fan-shaped beam; a detector element array comprising a plurality of detector element rows arranged side by side in the thickness direction of the fan-shaped beam, each of which detector element rows comprises a plurality of X-ray detector elements disposed in line in the extent direction of the fan-shaped beam; error detecting means for detecting an error between an impingement position of the fan-shaped beam and a predetermined impingement position in the direction of the side-by-side arrangement of the detector element rows on the detector element array; and control means for controlling the collimator based on the detected error so that the impingement position of the fan-shaped beam coincides with the predetermined impingement position.

(3) In still another aspect for solving the aforementioned problem, the present invention is an X-ray CT apparatus, comprising: an X-ray tube for generating X-rays emanating from a focus; a collimator for forming the X-rays into a fan-shaped beam; a detector element array comprising a plurality of detector element rows arranged side by side in the thickness direction of the fan-shaped beam, each of which detector element rows comprises a plurality of X-ray detector elements disposed in line in the extent direction of the fan-shaped beam; an error detecting apparatus for detecting an error between an impingement position of the fan-shaped beam and a predetermined impingement position in the direction of the side-by-side arrangement of the detector element rows on the detector element array; a control apparatus for controlling the collimator based on the detected error so that the impingement position of the fan-shaped beam coincides with the predetermined impingement position; a signal acquiring apparatus for acquiring X-ray detected signals for a plurality of views with an X-ray emitting/detecting system including the X-ray tube, the collimator and the detector element array rotated around an axis that is in parallel with the thickness direction of the fan-shaped beam; and a tomographic image producing apparatus for producing tomographic images for slices crossed by the fan-shaped beam based on the X-ray detected signals.

In the invention of the aspects described in (1)–(3), since an error in an impingement position of an X-ray beam is detected in the direction of the side-by-side arrangement of the detector element rows on the detector element array, and the collimator is controlled based on the detected error so that the impingement position of the X-ray beam coincides with a predetermined impingement position, the X-ray impingement position can be kept constant on the detector element array.

In the invention of these aspects, it is preferred to detect the error based on a ratio of a difference between X-ray detected signals to a sum of those X-ray detected signals, which X-ray detected signals are detected by X-ray detector elements that are adjacent in the direction of the side-by-side arrangement of the detector element rows, because an error measurement can be obtained independent of the magnitude of the X-ray detected signals.

(4) In still another aspect for solving the aforementioned problem, the present invention is a collimator control method, comprising the steps of: forming X-rays emanating from a focus of an X-ray tube into a fan-shaped beam by a collimator, and projecting the fan-shaped beam onto a detector element array comprising a plurality of detector element rows arranged side by side in the thickness direction of the fan-shaped beam, each of which detector element rows comprises a plurality of X-ray detector elements disposed in line in the extent direction of the fan-shaped beam; detecting an error between an impingement position of the fan-shaped beam and a predetermined impingement position in the direction of the side-by-side arrangement of the detector element rows on the detector element array; and controlling the collimator based on the detected error so that the impingement position of the fan-shaped beam coincides with the predetermined impingement position, wherein no control is performed when the error falls within a first range, the control is performed with a first proportional gain when the error exceeds the first range and falls within a second range larger than the first range, and the control is performed with a second proportional gain larger than the first proportional gain when the error exceeds the second range.

(5) In still another aspect for solving the aforementioned problem, the present invention is a collimator control apparatus, comprising: an X-ray tube for generating X-rays emanating from a focus; a collimator for forming the X-rays into a fan-shaped beam; a detector element array comprising a plurality of detector element rows arranged side by side in the thickness direction of the fan-shaped beam, each of which detector element rows comprises a plurality of X-ray detector elements disposed in line in the extent direction of the fan-shaped beam; error detecting means for detecting an error between an impingement position of the fan-shaped beam and a predetermined impingement position in the direction of the side-by-side arrangement of the detector element rows on the detector element array; and control means for controlling the collimator based on the detected error so that the impingement position of the fan-shaped beam coincides with the predetermined impingement position, wherein the control means performs no control when the error falls within a first range, performs the control with a first proportional gain when the error exceeds the first range and falls within a second range larger than the first range, and performs the control with a second proportional gain larger than the first proportional gain when the error exceeds the second range.

(6) In still another aspect for solving the aforementioned problem, the present invention is an X-ray CT apparatus, comprising: an X-ray tube for generating X-rays emanating from a focus; a collimator for forming the X-rays into a fan-shaped beam; a detector element array comprising a plurality of detector element rows arranged side by side in the thickness direction of the fan-shaped beam, each of which detector element rows comprises a plurality of X-ray detector elements disposed in line in the extent direction of the fan-shaped beam; an error detecting apparatus for detecting an error between an impingement position of the fan-shaped beam and a predetermined impingement position in the direction of the side-by-side arrangement of the detector element rows on the detector element array; a control apparatus for controlling the collimator based on the detected error so that the impingement position of the fan-shaped beam coincides with the predetermined impingement position, wherein the control apparatus performs no control when the error falls within a first range, performs the control with a first proportional gain when the error exceeds the first range and falls within a second range larger than the first range, and performs the control with a second proportional gain larger than the first proportional gain when the error exceeds the second range; a signal acquiring apparatus for acquiring X-ray detected signals for a plurality of views with an X-ray emitting/detecting system including the X-ray tube, the collimator and the detector element array rotated around an axis that is in parallel with the thickness direction of the fan-shaped beam; and a tomographic image producing apparatus for producing tomographic images for slices crossed by the: fan-shaped beam based on the X-ray detected signals.

In the invention of the aspects described in (4)–(6), since, in detecting an error in an impingement position of an X-ray beam in the direction of the side-by-side arrangement of the detector element rows on the detector element array, and controlling the collimator based on the detected error so that the impingement position of the X-ray beam coincides with a predetermined impingement position, no control is performed when the error falls within a first range, the control is performed with a first proportional gain when the error exceeds the first range and falls within a second range larger than the first range, and the control is performed with a second proportional gain larger than the first proportional gain when the error exceeds the second range, the control to keep a constant X-ray impingement position on the detector element array can be carried out rapidly and stably.

In the invention of these aspects, it is preferred to detect the error based on a ratio of a difference between X-ray detected signals to a sum of those X-ray detected signals, which X-ray detected signals are detected by X-ray detector elements that are adjacent in the direction of the side-by-side arrangement of the detector element rows, because an error measurement can be obtained independent of the magnitude of the X-ray detected signals.

(7) In still another aspect for solving the aforementioned problem, the present invention is a collimator control method, comprising the steps of: forming X-rays emanating from a focus of an X-ray tube into a fan-shaped beam by a collimator, and projecting the fan-shaped beam onto a detector element array comprising a plurality of detector element rows arranged side by side in the thickness direction of the fan-shaped beam, each of which detector element rows comprises a plurality of X-ray detector elements disposed in line in the extent direction of the fan-shaped beam; detecting an error between an impingement position of the fan-shaped beam and a predetermined impingement position in the direction of the side-by-side arrangement of the detector element rows on the detector element array; removing high frequency components in the detected error; and controlling the collimator based on the error after the removal of the high frequency components so that the impingement position of the fan-shaped beam coincides with the predetermined impingement position.

(8) In still another aspect for solving the aforementioned problem, the present invention is a collimator control apparatus, comprising: an X-ray tube for generating X-rays emanating from a focus; a collimator for forming the X-rays into a fan-shaped beam; a detector element array comprising a plurality of detector element rows arranged side by side in the thickness direction of the fan-shaped beam, each of which detector element rows comprises a plurality of X-ray detector elements disposed in line in the extent direction of the fan-shaped beam; error detecting means for detecting an error between an impingement position of the fan-shaped beam and a predetermined impingement position in the direction of the side-by-side arrangement of the detector element rows on the detector element array; high frequency component removing means for removing high frequency components in the detected error; and control means for controlling the collimator based on the error after the removal of the high frequency components so that the impingement position of the fan-shaped beam coincides with the predetermined impingement position.

(9) In still another aspect for solving the aforementioned problem, the present invention is an X-ray CT apparatus, comprising: an X-ray tube for generating X-rays emanating from a focus; a collimator for forming the X-rays into a fan-shaped beam; a detector element array comprising a plurality of detector element rows arranged side by side in the thickness direction of the fan-shaped beam, each of which detector element rows comprises a plurality of X-ray detector elements disposed in line in the extent direction of the fan-shaped beam; an error detecting apparatus for detecting an error between an impingement position of the fan-shaped beam and a predetermined impingement position in the direction of the side-by-side arrangement of the detector element rows on the detector element array; a high frequency component removing apparatus for removing high frequency components in the detected error; a control apparatus for controlling the collimator based on the error after the removal of the high frequency components so that the impingement position of the fan-shaped beam coincides with the predetermined impingement position; a signal acquiring apparatus for acquiring X-ray detected signals for a plurality of views with an X-ray emitting/detecting system including the X-ray tube, the collimator and the detector element array rotated around an axis that is in parallel with the thickness direction of the fan-shaped beam; and a tomographic image producing apparatus for producing tomographic images for slices crossed by the fan-shaped beam based on the X-ray detected signals.

In the invention of the aspects described in (7)–(9), since an error in an impingement position of an X-ray beam is detected in the direction of the side-by-side arrangement of the detector element rows on the detector element array, and the collimator is controlled based on the error with its high frequency components removed so that the impingement position of the X-ray beam coincides with a predetermined impingement position, the X-ray impingement position can be kept constant on the detector element array without being affected by the high frequency components in the error.

In the invention of these aspects, it is preferred to detect the error based on a ratio of a difference between X-ray detected signals to a sum of the X-ray detected signals, which X-ray detected signals are detected by X-ray detector elements that are adjacent in the direction of the side-by-side arrangement of the detector element rows, because an error measurement can be obtained independent of the magnitude of the X-ray detected signals.

Moreover, the removal of high frequency components may be achieved either by averaging processing or by low-pass filtering.

(10) In still another aspect for solving the aforementioned problem, the present invention is a collimator control method, comprising the steps of: forming X-rays emanating from a focus of an X-ray tube into a fan-shaped beam by a collimator, and projecting the fan-shaped beam onto a detector element array comprising a plurality of detector element rows arranged side by side in the thickness direction of the fan-shaped beam, each of which detector element rows comprises a plurality of X-ray detector elements disposed in line in the extent direction of the fan-shaped beam; detecting an error between an impingement position of the fan-shaped beam and a predetermined impingement position in the direction of the side-by-side arrangement of the detector element rows on the detector element array; removing high frequency components in the detected error; and controlling the collimator based on the error after the removal of the high frequency components so that the impingement position of the fan-shaped beam coincides with the predetermined- impingement position, wherein no control is performed when the error falls within a first range, the control is performed with a first proportional gain when the error exceeds the first range and falls within a second range larger than the first range, and the control is performed with a second proportional gain larger than the first proportional gain when the error exceeds the second range.

(11) In still another aspect for solving the aforementioned problem, the present invention is a collimator control apparatus, comprising: an X-ray tube for generating X-rays emanating from a focus; a collimator for forming the X-rays into a fan-shaped beam; a detector element array comprising a plurality of detector element rows arranged side by side in the thickness direction of the fan-shaped beam, each of which detector element rows comprises a plurality of X-ray detector elements disposed in line in the extent direction of the fan-shaped beam; error detecting means for detecting an error between an impingement position of the fan-shaped beam and a predetermined impingement position in the direction of the side-by-side arrangement of the detector element rows on the detector element array; high frequency component removing means for removing high frequency components in the detected error; and control means for controlling the collimator based on the error after the removal of the high frequency components so that the impingement position of the fan-shaped beam coincides with the predetermined impingement position, wherein the control means performs no control when the error falls within a first range, performs the control with a first proportional gain when the error exceeds the first range and falls within a second range larger than the first range, and performs the control with a second proportional gain larger than the first proportional gain when the error exceeds the second range.

(12) In still another aspect for solving the aforementioned problem, the present invention is an X-ray CT apparatus, comprising: an X-ray tube for generating X-rays emanating from a focus; a collimator for forming the X-rays into a fan-shaped beam; a detector element array comprising a plurality of detector element rows arranged side by side in the thickness direction of the fan-shaped beam, each of which detector element rows comprises a plurality of X-ray detector elements disposed in line in the extent direction of the fan-shaped beam; an error detecting apparatus for detecting an error between an impingement position of the fan-shaped beam and a predetermined impingement position in the direction of the side-by-side arrangement, of the detector element rows on the detector element array; a high frequency component removing apparatus for removing high frequency components in the detected error; a control apparatus for controlling the collimator based on the error after the removal of the high frequency components so that the impingement position of the fan-shaped beam coincides with the predetermined impingement position, wherein the control means performs no control when the error falls within a first range, performs the control with a first proportional gain when the error exceeds the first range and falls within a second range larger than the first range, and performs the control with a second proportional gain larger than the first proportional gain when the error exceeds the second range; a signal acquiring apparatus for acquiring X-ray detected signals for a plurality of views with an X-ray emitting/detecting system including the X-ray tube, the collimator and the detector element array rotated around an axis that is in parallel with the thickness direction of the fan-shaped beam; and a tomographic image producing apparatus for producing tomographic images for slices crossed by the fan-shaped beam based on the X-ray detected signals.

In the invention of the aspects described in (10)–(12), since, in detecting an error in an impingement position of an X-ray beam in the direction of the side-by-side, arrangement of the detector element rows on the detector element array, and controlling the collimator based on the error with its high frequency components removed so that the impingement position of the X-ray beam coincides with a predetermined impingement position, no control is performed when the error falls within a first range, the control is performed with a first proportional gain when the error exceeds the first range and falls within a second range larger than the first range, and the control is performed with a second proportional gain larger than the first proportional gain when the error exceeds the second range, the control to keep a constant X-ray impingement position on the detector element array can be carried out rapidly and stably without being affected by the high frequency components in the error.

In the invention of these aspects, it is preferred to detect the error based on a ratio of a difference between X-ray detected signals to a sum of the X-ray detected signals, which X-ray detected signals are detected by X-ray detector elements that are adjacent in the direction of the side-by-side arrangement of the detector element rows, because error measurement can be obtained independent of the magnitude of the X-ray detected signals.

Moreover, the removal of high frequency components may be achieved either by averaging processing or by low-pass filtering.

As described above in detail, the present invention can provide a collimator control method and apparatus for keeping a constant X-ray impingement position on an X-ray detector, and an X-ray CT apparatus comprising such a collimator control apparatus.

Further objects and advantages of the present invention will be apparent from the following description of the preferred embodiments of the invention as illustrated in the accompanying drawings.

BRIEF DESCRIPTION OF THE DRAWINGS

FIG. 2 is a schematic view of a detector array in the apparatus shown in FIG. 1.

FIGS. 3–6 are schematic diagrams of an X-ray emitting/detecting apparatus in the apparatus shown in FIG. 1.

DETAILED DESCRIPTION OF THE INVENTION

Figure 1:
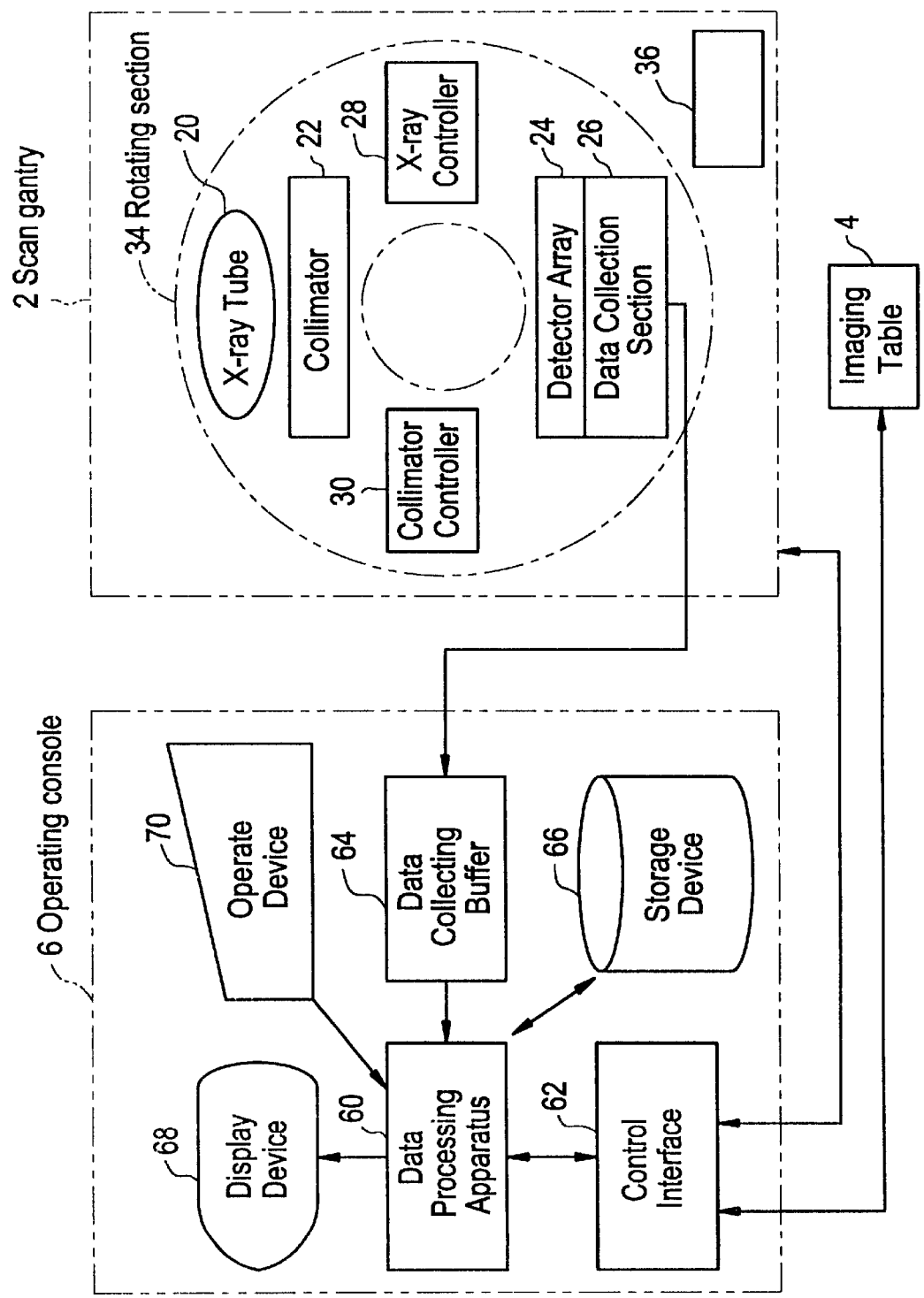
FIG. 1 is a block diagram of an apparatus in accordance with one embodiment of the present invention.

Several embodiments of the present invention will now be described in detail with reference to the accompanying drawings. It should be noted that the present invention is not limited to these embodiments. FIG. 1 is a block diagram of an X-ray CT apparatus, which is an embodiment of the present invention. The configuration of the apparatus represents an embodiment of the apparatus in accordance with the present invention. The operation of the apparatus represents an embodiment of the method in accordance with the present invention.

As shown in FIG. 1, the apparatus comprises a scan gantry 2, an imaging table 4 and an operating console 6. The scan gantry 2 is an embodiment of the signal acquiring apparatus of the present invention. The scan gantry 2 has an X-ray tube 20. The X-ray tube 20 is an embodiment of the X-ray tube of the present invention. X-rays (not shown) emitted from the X-ray tube 20 are formed into, for example, a fan-shaped X-ray beam, i.e., a fan beam, by a collimator 22, and projected onto a detector array 24. The collimator 22 is an embodiment of the collimator of the present invention.

The detector array 24 has a plurality of X-ray detector elements arranged in line as an array in the extent direction of the fan-shaped X-ray beam. The detector array 24 is an embodiment of the detector element array of the present invention. The configuration of the detector array 24 will be described in detail later. The X-ray tube 20, collimator 22 and detector array 24 together constitute an X-ray emitting/detecting apparatus, which will be described in detail later.

The detector array 24 is connected with a data collecting section 26 for collecting data detected by the individual X-ray detector elements in the detector array 24. The emission of the X-rays from the X-ray tube 20 is controlled by an X-ray controller 28. The connection relationship between the X-ray tube 20 and the X-ray controller 28 is omitted in the drawing. The collimator 22 is controlled by a collimator controller 30. The connection relationship between the collimator 22 and the collimator controller 30 is omitted in the drawing.

The above-described components from the X-ray tube 20 through the collimator controller 30 are mounted on a rotating section 34 of the scan gantry 2. The rotation of the rotating section 34 is controlled by a rotation controller 36. The connection relationship between the rotating section 34 and the rotation controller 36 is omitted in the drawing.

The imaging table 4 is intended to carry an object to be imaged (not shown) into and out of an X-ray irradiation space in the scan gantry 2. The relationship between the object and the X-ray irradiation space will be described in detail later.

The operating console 6 has a data processing apparatus 60, which is comprised of, for example, a computer. The data processing apparatus 60 is connected with a control interface 62, which is in turn connected with the scan gantry 2 and the imaging table 4. The data processing apparatus 60 controls the scan gantry 2 and the imaging table 4 via the control interface 62.

The data collecting section 26, X-ray controller 28, collimator controller 30 and rotation controller 36 in the scan gantry 2 are controlled via the control interface 62. The individual connections between these sections and the control interface 62 are omitted in the drawing.

The data processing apparatus 60 is also connected with a data collection buffer 64, which is in turn connected with the data collecting section 26 in the scan gantry 2. Data collected at the data collecting section 26 is input to the data processing apparatus 60 via the data collection buffer 64.

The data processing apparatus 60 performs image reconstruction using signals of the transmitted X-rays for a plurality of views collected via the data collection buffer 64. The image reconstruction is performed using a filtered back projection technique, for example. The data processing apparatus 60 is an embodiment of the tomographic image producing apparatus of the present invention.

The data processing apparatus 60 is also connected with a storage device 66 for storing several kinds of data, reconstructed images, programs for implementing the functions of the present apparatus, and so forth.

The data processing apparatus 60 is moreover connected with a display device 68 that displays the reconstructed image and other information output from the data processing apparatus 60, and an operating device 70 that is operated by a user supplying several instructions and information to the data processing apparatus 60. The user interactively operates the present apparatus using the display device 68 and the operating device 70.

FIG. 2 schematically shows a configuration of the detector array 24. As shown, the detector array 24 is a multi-channel X-ray detector having a plurality of X-ray detector elements 24(ik) arranged in an array.

The plurality of the X-ray detector elements 24(ik) together form an X-ray impingement surface, curved as a cylindrical concavity. Reference symbol 'i' designates a channel index and 'i'=1–1,000, for example. Reference symbol 'k' designates a row index and 'k'=1, 2, for example. The X-ray detector elements 24(ik) that have the same row index 'k' together constitute a detector element row. The detector array 24 is not limited to having two rows, but may have more than two rows divided into two groups. Although the description will be made on an example the detector array 24 having two rows hereinbelow, the same holds for a detector array having more rows.

A certain number of channels at the ends of the detector array 24 are reference channels 25 in each row. The reference channels 25 are situated outside a range of the object that is projected in imaging.

Each X-ray detector element 24(ik) is formed of a combination of a scintillator and a photodiode, for example. It should be noted that the X-ray detector element 24(ik) is not limited thereto but may be a semiconductor X-ray detector element using cadmium telluride (CdTe) or the like, or an ionization chamber X-ray detector element using xenon (Xe) gas, for example.

FIG. 3 illustrates a relationship among the X-ray tube 20, collimator 22 and detector array 24 in the X-ray emitting/detecting apparatus. FIG. 3(a) is a view from the front of the scan gantry 2 and (b) is a view from the side of the scan gantry 2. As shown, the X-rays emitted from the X-ray tube 20 are formed into a fan-shaped X-ray beam 400 by the collimator 22, and projected onto the detector array 24.

In FIG. 3(a), the extent of the fan-shaped X-ray beam 400 is illustrated. The extent direction of the X-ray beam 400 is identical to the direction of the linear arrangement of the channels in the detector array 24. In FIG. 3(b), the thickness of the X-ray beam 400 is illustrated. The thickness direction of the X-ray beam 400 is identical to the direction of the side-by-side arrangement (k-direction) of the rows in the detector array 24.

Figure 4:
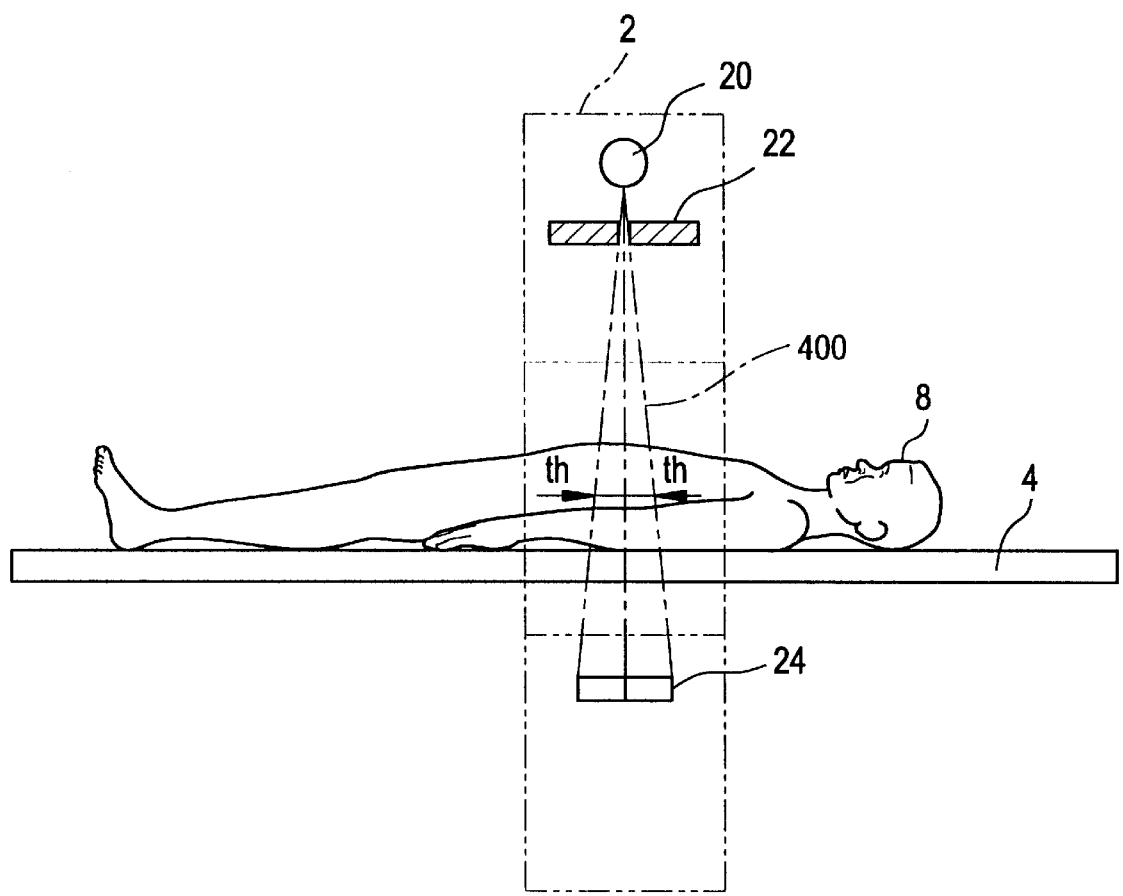

An object 8 placed on the imaging table 4 is carried into the X-ray irradiation space with the object's body axis intersecting the fan surface of such an X-ray beam 400, as exemplarily shown in FIG. 4. The scan gantry 2 has a cylindrical structure containing therein the X-ray emitting/detecting apparatus.

The X-ray irradiation space is formed in the internal space of the cylindrical structure of the scan gantry 2. An image of the object 8 sliced by the X-ray beam 400 is projected on the detector array 24. The X-rays after passing through the object 8 are detected by the detector array 24. The slice thickness 'th' of the X-ray beam 400 penetrating the object 8 is regulated by the openness of an aperture of the collimator 22.

The X-ray emitting/detecting apparatus consisting of the X-ray tube 20, collimator 22 and detector array 24 rotates (or scans) around the body axis of the object 8 while maintaining their mutual relationships. Projection data for a plurality of (for example, ca. 1,000) views are collected per scan rotation. The collection of the projection data is performed by a system of the detector array 24, data collecting section 26 and data collection buffer 64.

Based on projection data of two slices collected in the data collection buffer 64, tomographic image production, or image reconstruction, for the two slices is performed by the data processing apparatus 60. The image reconstruction is carried out such as by processing the projection data for, for example, 1,000 views obtained by one scan rotation by the filtered back projection technique.

Figure 5:
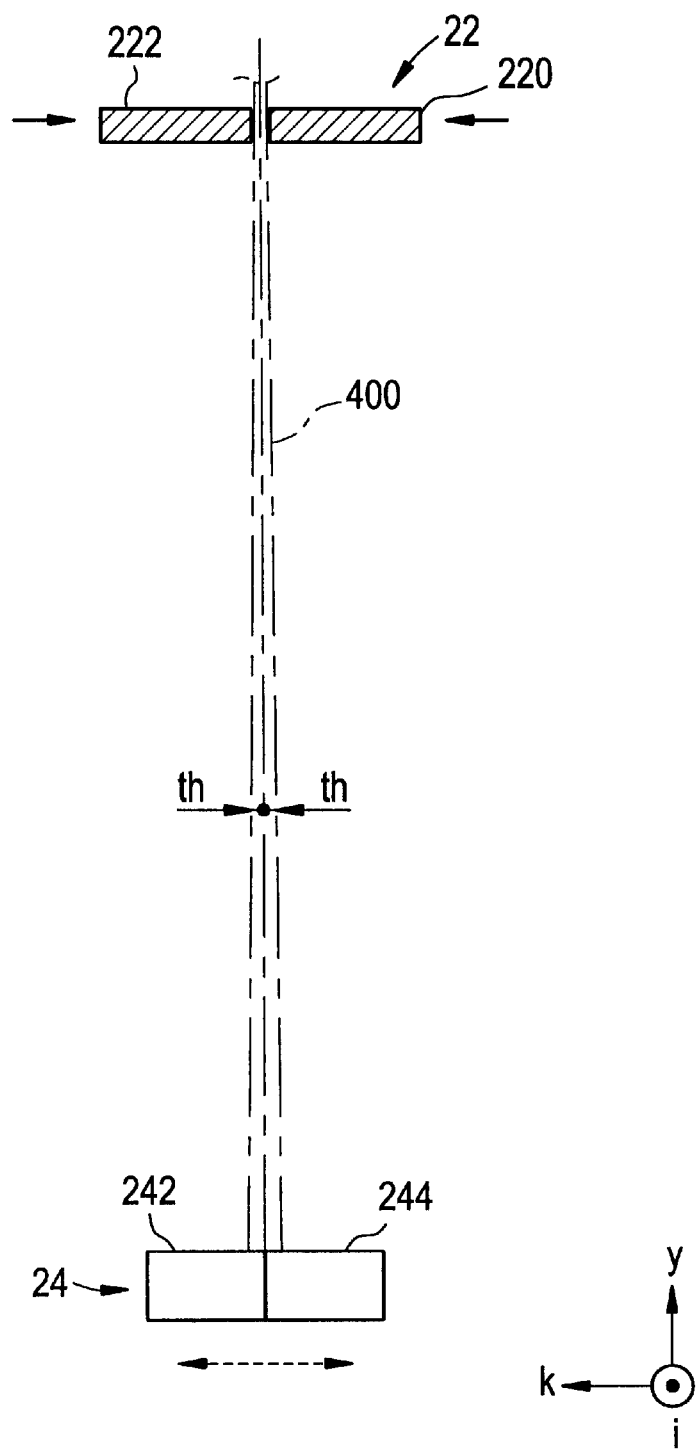
Figure 6:
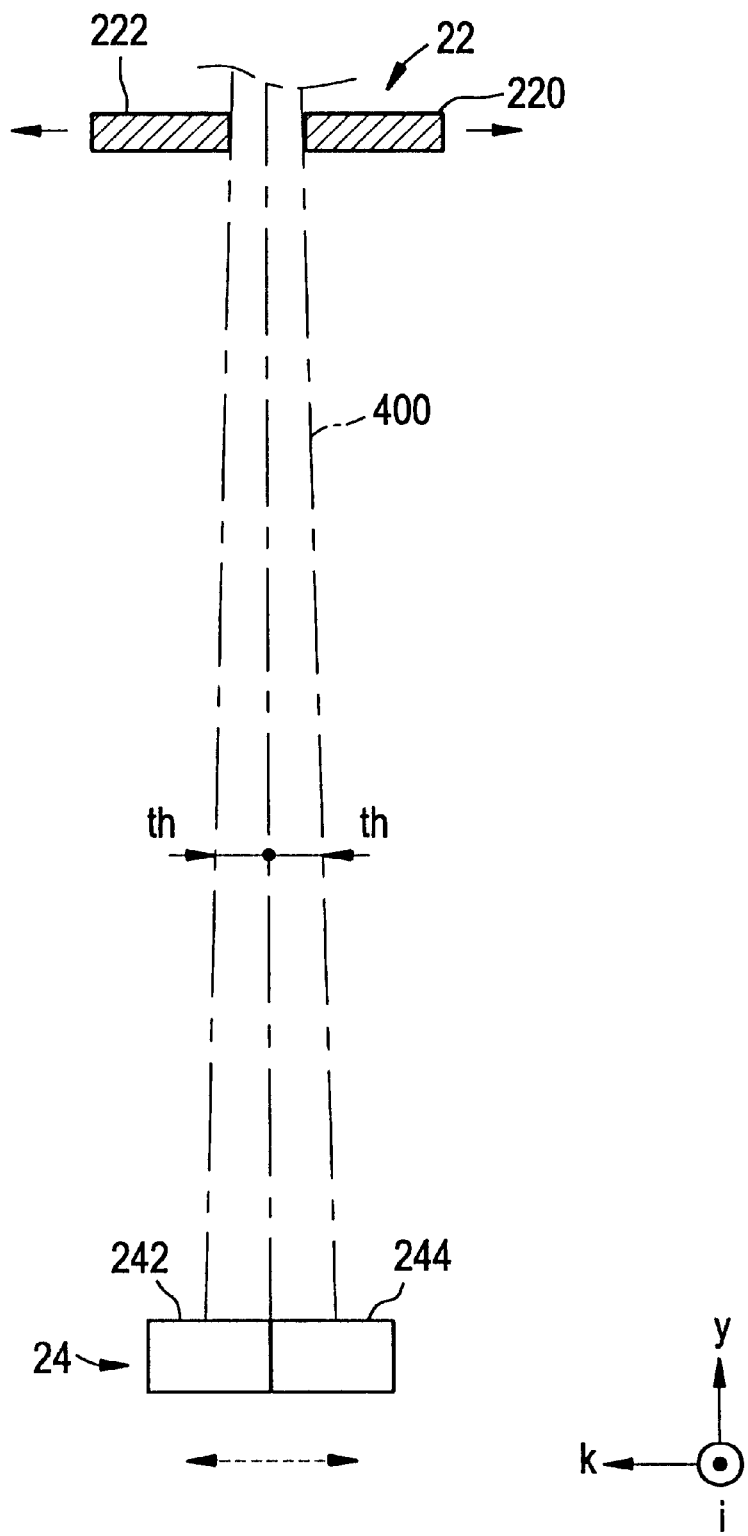

FIGS. 5 and 6 are schematic diagrams illustrating the X-ray beam 400 projected onto the detector array 24 in more detail. As shown in FIG. 5, the slice thickness 'th' of a projection image on the X-ray detectors 242 and 244 is reduced by shifting collimator blocks 220 and 222 in the collimator 22 in a direction such that the aperture is narrowed.

Similarly, as shown in FIG. 6, the slice thickness 'th' is increased by moving the collimator blocks 220 and 222 in a direction such that the aperture is widened. Such regulation of the slice thickness is achieved by the collimator controller 30 under the direction of the data processing apparatus 60.

Moreover, the impingement position on the detector array 24 in the k-direction is adjusted by simultaneously moving both the collimator blocks 220 and 224 defining the slice thickness 'th' in the k-direction while maintaining their relative positional relationship. The variation in the impingement position associated with the X-ray focus shift can thus be corrected and automatically controlled so that the X-ray beam 400 is always projected onto a constant position.

The adjustment of the impingement position in the k-direction may be achieved by shifting the detector array 24 relative to the collimator 22 in the k-direction, as shown by broken arrow, instead of moving the collimator blocks 220 and 222. This allows the mechanism for the slice thickness adjustment and the mechanism for the impingement position control in the thickness direction to be separately provided, thereby allowing diversified control.

On the other hand, if all such mechanisms are implemented by the collimator 22, the system for the control can be integrated and desired simplification of configuration can be fulfilled. It will be easily recognized that these two types of means may be combined to perform the impingement position adjustment. Such a function for automatically controlling the impingement position will be sometimes referred to as an auto collimator hereinbelow.

Figure 7:
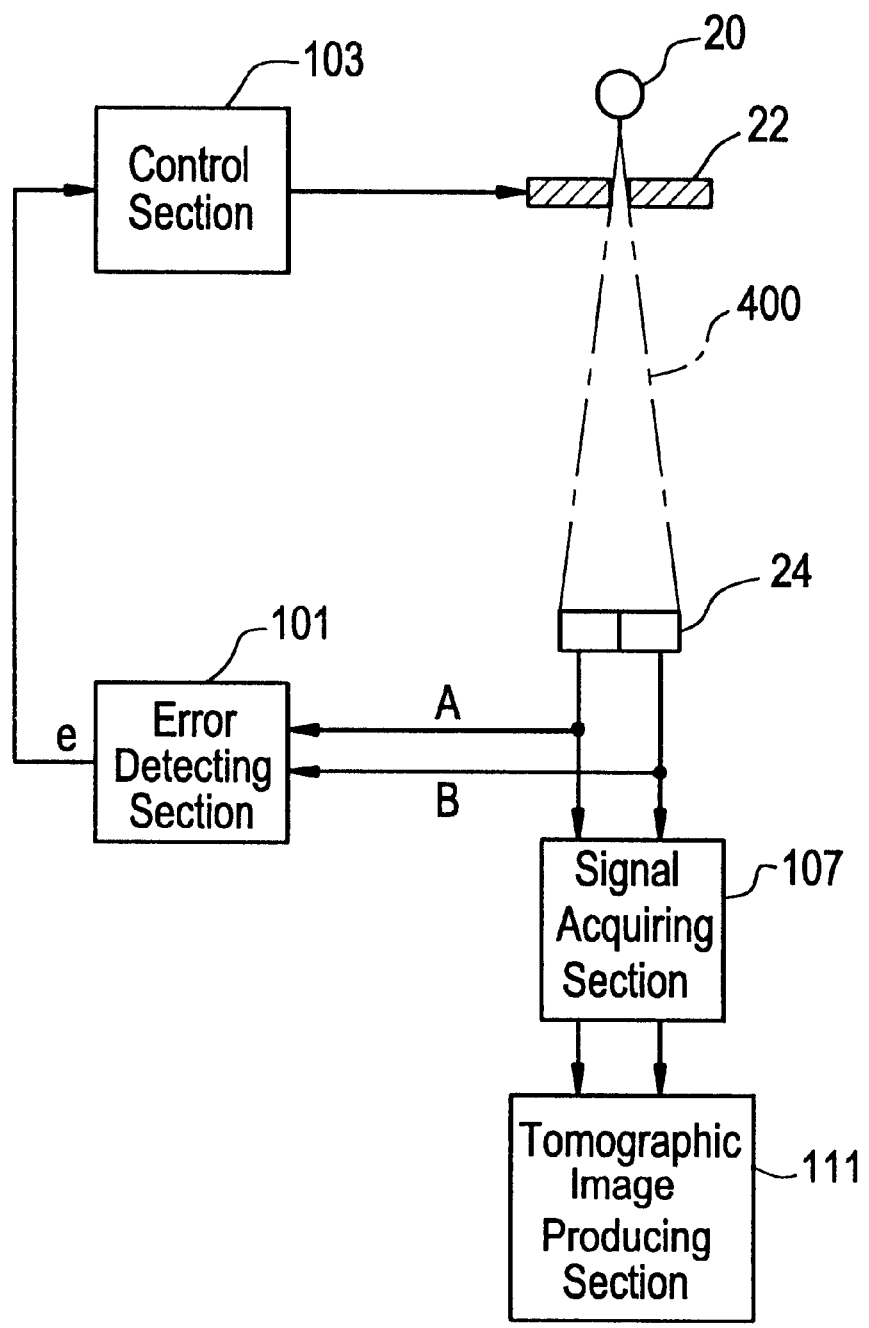
FIG. 7 is a block diagram of an apparatus in accordance with one embodiment of the present invention.

FIG. 7 shows a block diagram of the present apparatus with respect to the auto collimator. An error of the impingement position of the X-ray beam 400 in the k-direction is detected by an error detecting section 101 as shown. The error detecting section 101 detects the impingement position error based on outputs from the reference channels 25 of the two rows in the detector array 24.

The error detection is performed by using X-ray detected signals A and B of the X-ray beam 400 from the reference channels 25 of the two rows to calculate the error 'e' from the following equation:

$$e = \frac{A - B}{A + B}. \tag{1}$$

An error measurement can thus be obtained independent of the magnitude of X-ray detected signals. The error detecting section 101 is implemented by a function of the data processing apparatus 60. The error detecting section 101 is an embodiment of the error detecting means of the present invention. It is also an embodiment of the error detecting apparatus of the present invention.

Figure 8:
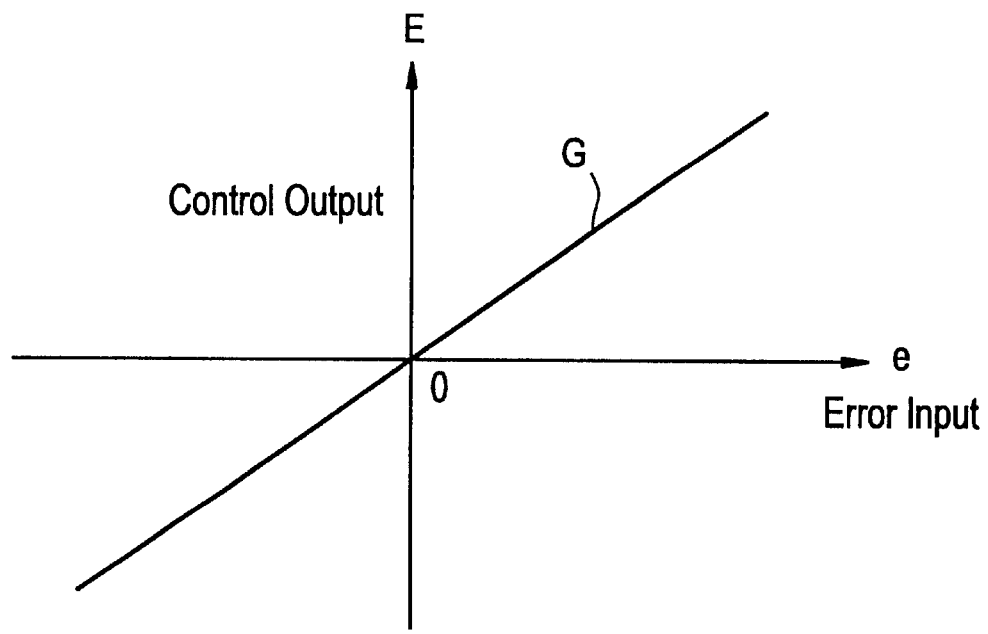
FIGS. 8 and 9 are graphs showing examples of a proportional gain for collimator control.

The error detecting signal is input to a control section 103. The control section 103 then feedback-controls the collimator 22 so that the error 'e' becomes zero. The control output from the control section 103 is proportional to the error 'e', as exemplarily shown in FIG. 8. The slope of this input-output characteristic curve represents a proportional gain G for the control. The proportional gain will be sometimes referred to simply as the gain hereinbelow.

When the error 'e' becomes zero, the following equation holds:

$$A = B. \tag{2}$$

That is, the X-ray beam 400 impinges equally upon the reference channels of the two rows. At this time, the X-ray beam 400 is projected equally divided between the two detector element rows in the detector array 24.

The control section 103 is implemented by functions of the data processing apparatus 60 and the collimator controller 30. The control section 103 is an embodiment of the control means of the present invention. It is also an embodiment of the control apparatus of the present invention.

The X-ray detected signals of the two detector element rows in the detector array 24 are collected at a signal acquiring section 107, and a tomographic image is produced at a tomographic image producing section 111 based on the collected signals. Thus, two tomographic images having equal slice thicknesses can be obtained.

The signal acquiring section 107 is implemented by the data collecting section 26, rotation controller 36 and data collection buffer 64. The signal acquiring section 107 is an embodiment of the signal acquiring apparatus of the present invention. The tomographic image producing section 111 is implemented by a function of the data processing apparatus 60. The tomographic image producing section 111 is an embodiment of the tomographic image producing apparatus of the present invention.

The gain of the control section 103 may be varied according to the error. Specifically, as exemplarily shown in FIG. 9, the gain is set to zero when $$|e| \leq \alpha_1, \tag{3}$$

the gain is set to G1 ($\neq 0$) when $$\alpha_1 < |e| \leq \alpha_2, \tag{4}$$

and the gain is set to G2 (>G1) when $$|e| > \alpha_2. \tag{5}$$

In the above equations, $\alpha 1$ is an allowed value of the error. It is also a first gain switch point. $\alpha 2$ is a second gain switch point.

Accordingly, the control is not performed when the error 'e' is equal to or less than the allowed value $\alpha 1$, that is, a 'neutral zone' can be provided. The control can thereby be stabilized. When the error 'e' is more than the allowed value $\alpha 1$ and is equal to or less than $\alpha 2$, the feedback control is performed with the gain G1 to draw the error 'e' back to the allowed value. When the error 'e' exceeds $\alpha 2$, the feedback is performed with the gain G2 larger than G1 to draw the error 'e' back more rapidly than with the control with G1.

Figure 9:
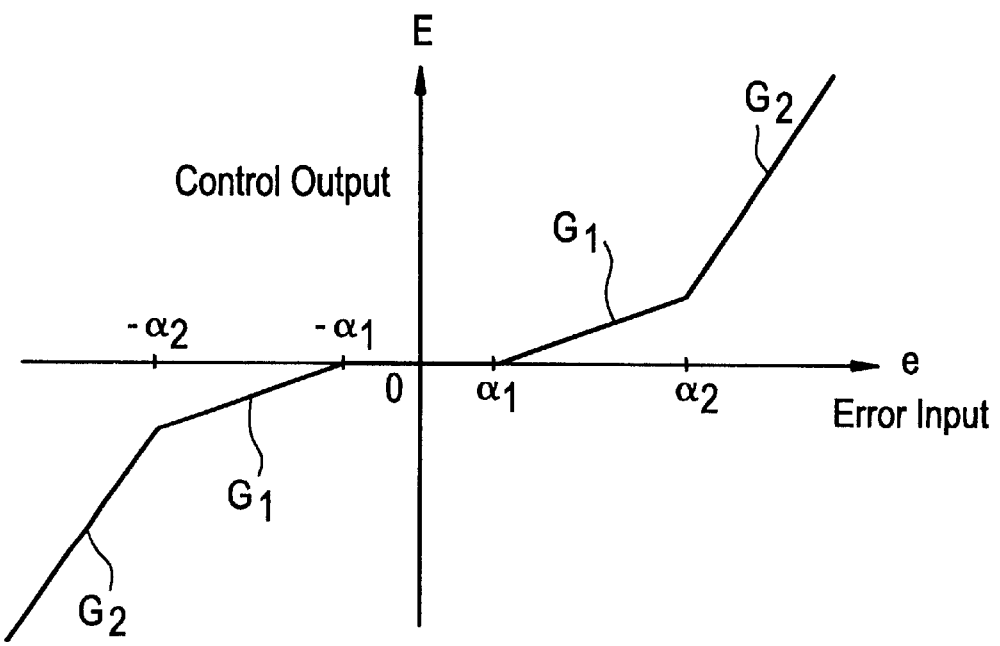

By thus varying the gain according to the error, collimator control possessing both stability and rapidity can be achieved. It should be noted that the switching of the gain is not limited to three steps as shown in FIG. 9, but may have two steps or more than three steps.

The error 'e' contains high frequency components. The high frequency components are primarily caused by very small fluctuations of the focus position incident to the rotation of the anode in the X-ray tube. Since the rotation of the anode occurs at high speed, for example, at about 8,000–12,000 rpm, the fluctuations of the focus contain the high frequency components. Since such fluctuations are extraneous to the displacement of the X-ray focus incident to the temperature change, control effected to follow such fluctuations is meaningless, or rather may degrade the stability of the control. Therefore, the high frequency components are removed prior to inputting the error 'e' to the control section 103 to further increase the stability of the control.

Figure 10:
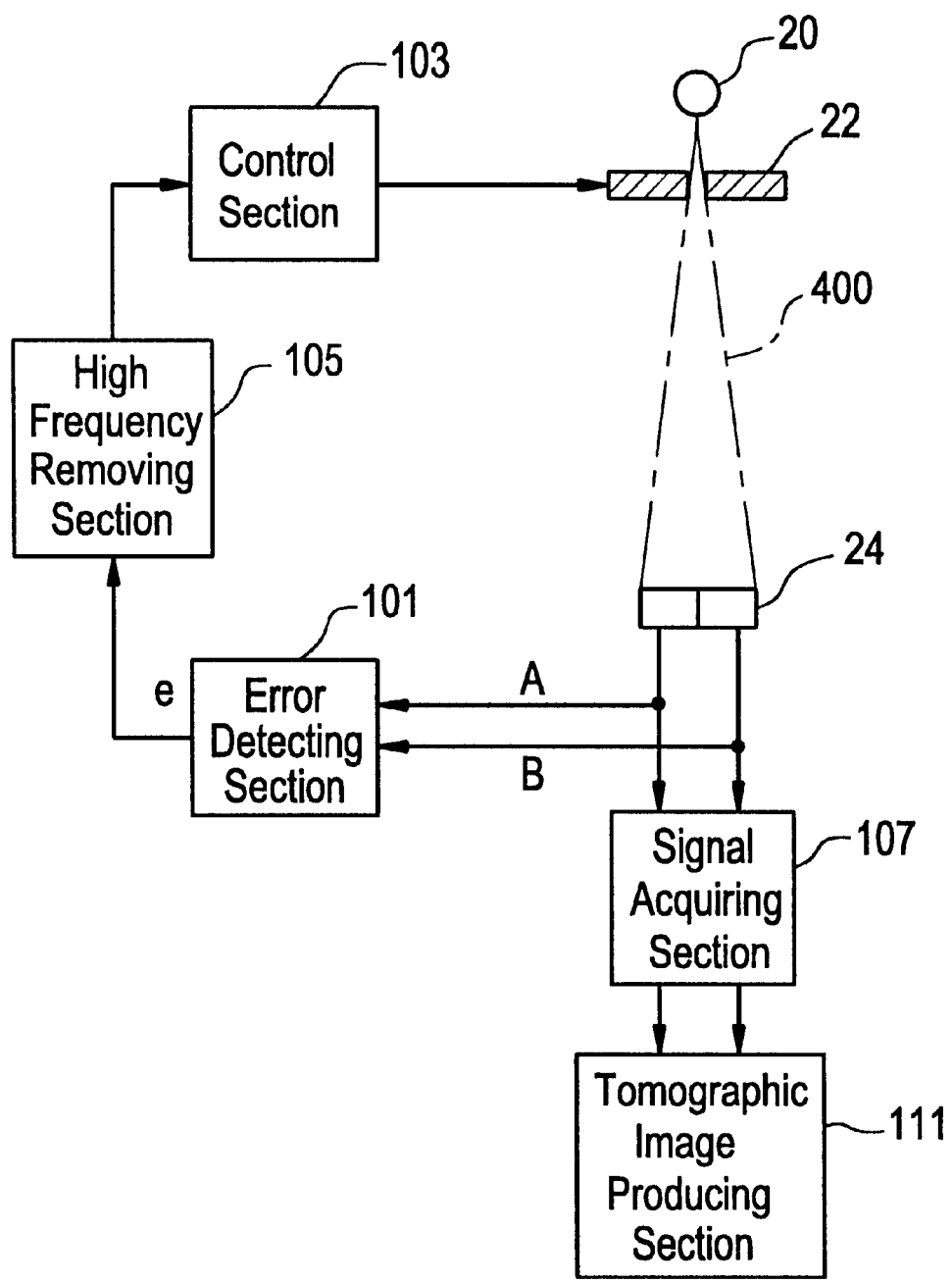
FIG. 10 is a block diagram of an apparatus in accordance with one embodiment of the present invention.

FIG. 10 shows a block diagram of the present apparatus provided with such high frequency component removal. Similar portions in FIG. 10 to those shown in FIG. 7 are designated by similar reference numerals and explanation thereof will be omitted.

As shown, a high frequency removing section 105 is situated between the error detecting section 101 and the control section 103. The high frequency removing section 105 removes the high frequency components in the error 'e' input from the error detecting section 101 and inputs an error signal not containing the high frequency components to the control section 103.

The high frequency removing section 105 is implemented by a function of the data processing apparatus 60. The high frequency removing section 105 is an embodiment of the high frequency component removing means of the present invention. It is also an embodiment of the high frequency component removing apparatus of the present invention.

The high frequency component removal in the high frequency removing section 105 is achieved by, for example, determining the average of data obtained in time series. A moving average value of, for example, 16 time-series data values is employed as the average. The number of data values for the moving averaging is not limited to 16 but may be any other appropriate one. The data of the error 'e' is obtained successively at the same timing as the view data. Therefore, the error 'e' is moving-averaged for, for example, every 16 views.

The moving averaging may be weighted by an appropriate weight instead of the simple moving averaging. Moreover, instead of the averaging, the removal of the high frequency components may be achieved by low-pass filtering of the data values of the time-series data.

By thus removing the high frequency components contained in the error 'e' by the high frequency removing section 105, the control of the impingement position can be stabilized. By stabilizing the impingement position, the slice thicknesses of two tomographic images become equal and stable, thus allowing images to be obtained with good quality.

Although the present invention has been described with reference to the preferred embodiments, several changes and substitutions may be made on these embodiments by those ordinarily skilled in the art without departing from the scope of the present invention. Therefore, the scope of the present invention is intended to encompass not only the aforementioned embodiments but all embodiments pertaining to the appended claims.

Many widely different embodiments of the invention may be configured without departing from the spirit and the scope of the present invention. It should be understood that the present invention is not limited to the specific embodiments described in the specification, except as defined in the appended claims.

What is claimed is:

1. A collimator control method, comprising the steps of:
   forming X-rays emanating from a focus of an X-ray tube into a fan shaped beam by a collimator and projecting said fan shaped beam onto a detector element array comprising a plurality of detector element rows arranged side by side in a thickness direction of said fan shaped beam, each of said detector element rows comprising a plurality of X-ray detector elements disposed in an extent direction of said fan shaped beams;
   detecting an error between an impingement position of said fan shaped beam and a predetermined impingement position in direction of said side by side arrangement of said detector element rows on said detector array;
   controlling said collimator based on said detected error so that said impingement position of said ran shaped beam coincides with said predetermined impingement position; and
   removing high frequency components in said detected error; and wherein
      said collimator is controlled based on said error after removal of said high frequency components so that said impingement position of said fan shaped beam coincides with said predetermined impingement position.

2. The method of claim 1, further comprising the step of:
   detecting said error based on ratio of difference between X-ray detected signals to a sum of said X-ray detected signals, said X-ray detected signals being detected by X-ray detector elements adjacent in direction of said side by side arrangement of said detector element rows.

3. The method of claim 1, wherein said high frequency components are removed by averaging.

4. The method of claim 1, wherein said high frequency components are removed by low pass filtering.

5. The method of claim 1, wherein
   no control is performed when said error falls within a first range;
   control is performed with a first proportional gain when said error exceeds said first range and falls within a second range larger than said first range; and
   control is performed with a second proportional gain larger than said first proportional gain when said error exceeds said second range.

6. The method of claim 5, further comprising the step of:
   detecting said error based on ratio of difference between X-ray detected signals to a sum of said X-ray detected signals, said X-ray detected signals being detected by X-ray detector elements adjacent in direction of said side by side arrangement of said detector element rows.

7. The method of claim 5, wherein said high frequency components are removed by averaging.

8. The method of claim 5, wherein said high frequency components are removed by low pass filtering.

9. A collimator control apparatus, comprising:
   an X-ray tube for generating X-rays emanating from a focus;
   a collimator for forming said X-rays into a fan shaped beam;
   a detector array comprising a plurality of detector element rows arranged side by side in a thickness direction of said fan shaped beam, each of said detector element rows comprising a plurality of X-ray detector elements disposed in an extent direction of said fan shaped beam;
   error detecting means for detecting an error between an impingement position of said fan shaped beam and a predetermined impingement position in direction of said side by side arrangement of said detector element rows on said detector element array;
   control means for controlling said collimator based on said detector error so that said impingement position on said fan shaped beam coincides with said predetermined impingement position; and
   high frequency component removing means for removing high frequency components in said detected signal; and wherein
      said control means comprises means for controlling said collimator based on said error after removal of said high frequency components so that said impingement position of said fan shaped beam coincides with said predetermined impingement position.

10. The apparatus of claim 9, wherein
   said error detecting means comprises means for detecting said error based on ratio of difference between X-ray detected signals to a sum of said X-ray detected signals, said X-ray detected signals being detected by X-ray detector elements adjacent in direction of said side by side arrangement of said detector element rows.

11. The apparatus of claim 9, wherein
   said high frequency component removing means comprises means for removing high frequency.components by averaging.

12. The apparatus of claim 9, wherein
   said high frequency component removing means comprises means for removing high frequency components by low pass filtering.

13. The apparatus of claim 9, wherein
   said control means comprises means for
      performing no control when said error falls within a first range;

performing control with a first proportional gain when said error exceeds said first range and falls within a second range larger than said first range; and performing control with a second proportional gain larger than said first proportional gain when said error exceeds said second range.

14. The apparatus of claim 13, wherein
said error detecting means comprises means for detecting said error based on ratio of difference between X-ray detected signals to a sum of said X-ray detected signals, said X-ray detected signals being detected by X-ray detector elements adjacent in direction of said side by side arrangement of said detector element rows.

15. The apparatus of claim 13, wherein
said high frequency component removing means comprises means for removing high frequency components by averaging.

16. The apparatus of claim 13, wherein
said high frequency component removing means comprises means for removing high frequency components by low pass filtering.

17. An X-ray CT apparatus, comprising:
an X-ray tube for generating X-rays emanating from a focus;
a collimator for forming said X-rays into a fan shaped beam;
a detector element array comprising a plurality of detector element rows arranged side by side in a thickness direction of said fan shaped beam, each of said detector element rows comprising a plurality of X-ray detector elements disposed in line in an extent direction of said fan shaped beam;
an error detecting means for detecting an error between an impingement position of said fan shaped beam and a predetermined impingement position in direction of said side by side arrangement of said detector element rows on said detector element array;
a control means for controlling said collimator based on said detected error so that said impingement position of said fan shaped beam coincides with said predetermined impingement position;
a signal acquiring means for acquiring X-ray detected signals for a plurality of views with an X-ray emitting/detecting system including said X-ray tube, said collimator and said detector element array, being rotated around an axis parallel with a thickness direction of said fan shaped beam;
a tomographic image producing means for producing tomographic images for slices crossed by said fan shaped beam on said X-ray detected signals; and
means for removing high frequency components in said detected error; and wherein
said control means comprises means for controlling said collimator based on said error after removal of said high frequency components so that impingement position of said fan shaped beam coincides with said predetermined impingement position.

18. The apparatus of claim 17, wherein
said error detecting means comprises means for detecting said error based on ratio of difference between X-ray detected signals to a sum of said X-ray detected signals, said X-ray detected signals being detected by X-ray detector elements adjacent in direction of said side by side arrangement of said detector element rows.

19. The apparatus of claim 17, wherein said means for removing high frequency components comprises means for removing high frequency components by averaging.

20. The apparatus of claim 17, wherein said means for removing high frequency components comprises means for removing high frequency components by low pass filtering.

21. The apparatus of claim 17, wherein
said control means comprises means for
performing no control when said error falls within a first range;
performing control with a first proportional gain when said error exceeds said first range and falls within a second range larger than said first range; and
performing control with a second proportional gain larger than said first proportional gain when said error exceeds said second range.

22. The apparatus of claim 21, wherein
said error detecting means comprises leans for detecting said error based on ratio of difference between X-ray detected signals to a sum of said X-ray detected signals, said X-ray detected signals being detected by X-ray detector elements adjacent in direction of said side by side arrangement of said detector element rows.

23. The apparatus of claim 21, wherein
said means for removing high frequency components comprises means for removing high frequency components by averaging.

24. The apparatus of claim 21, wherein
said means for removing high frequency components comprises means for removing high frequency components by low pass filtering.

25. A collimator control method, comprising the steps of:
forming X-rays emanating from a focus of an X-ray tube into a fan shaped beam by a collimator and projecting said fan shaped beam unto a detector element array comprising a plurality of detector element rows arranged side by side in a thickness direction of said fan shaped beam, each of said detector element rows comprising a plurality of X-ray detector elements disposed in an extent direction of said fan shaped beam;
detecting an error between an impingement position of said fan shaped beam and a predetermined impingement position in direction of said side by side arrangement of said detector element rows on said detector array, said error being based on a ratio of difference between X-ray detected signals to sum of said X-ray detected signals; and
controlling said collimator based on said detected error so that said impingement position of said fan shaped beam coincides with said predetermined impingement position, wherein
no control is performed when said error falls within a first range,
control is performed with a first proportional gain when said error exceeds said first range and falls within a second range larger than said first range, and
control is performed with a second proportional gain larger than said first proportional gain when said error exceeds said second range, whereby control is stable and rapid.

26. A collimator control apparatus comprising:
means for forming X-rays emanating from a focus of an X-ray tube into a fan shaped beam by a collimator and projecting said fan shaped beam onto a detector element array comprising a plurality of detector element rows arranged side by side in a thickness direction of said fan shaped beam, each of said detector element rows comprising a plurality of X-ray detector elements disposed in an extent direction of said fan shaped beam;

means for detecting an error between an impingement position of said fan shaped beam and a predetermined impingement position in direction of said side by side arrangement of said detector element rows on said detector array, said error being based on a ratio of difference between X-ray detected signals to sum of said X-ray detected signals; and means for controlling said collimator based on said detected error so that said impingement position of said fan shaped beam coincides with said predetermined impingement position, wherein no control is performed when said error falls within a first range, control is performed with a first proportional gain when said error exceeds said first range and falls within a second range larger than said first range, and control is performed with a second proportional gain larger than said first proportional gain when said error exceeds said second range, whereby control is stable and rapid.

* * * * *